United States Patent [19]

Coleman et al.

[11] 4,275,081

[45] Jun. 23, 1981

[54] FAT PROCESS AND COMPOSITION

[75] Inventors: Michael H. Coleman, Bedford; Alasdair R. Macrae, Oakley, both of England

[73] Assignee: Lever Brothers Company, New York, N.Y.

[21] Appl. No.: 46,523

[22] Filed: Jun. 7, 1979

Related U.S. Application Data

[63] Continuation of Ser. No. 846,303, Oct. 28, 1977, abandoned, which is a continuation of Ser. No. 766,117, Feb. 7, 1977, abandoned.

[30] Foreign Application Priority Data

Feb. 11, 1976 [GB] United Kingdom ................ 5376/76

[51] Int. Cl.$^3$ ........................... A23D 5/00; C12P 7/64
[52] U.S. Cl. ...................................... 426/33; 426/35; 426/601; 435/134
[58] Field of Search .................... 846/303; 426/33, 35, 426/601, 607, 631, 660; 435/134, 271

[56] References Cited

U.S. PATENT DOCUMENTS

| | | | |
|---|---|---|---|
| 2,485,779 | 10/1949 | Sanders | 435/271 |
| 2,769,750 | 11/1956 | Harris | 435/248 |
| 2,924,555 | 2/1960 | Reese | 435/74 |
| 3,012,890 | 12/1961 | Dutton et al. | 426/607 X |
| 3,190,753 | 6/1965 | Claus et al. | 426/35 X |
| 3,492,130 | 1/1970 | Harwood | 426/607 |
| 3,878,231 | 4/1975 | Harwood | 426/607 X |
| 4,032,405 | 6/1977 | Tatsumi et al. | 435/134 X |

OTHER PUBLICATIONS

Alford, J. A. et al., "Jour. Lipid Res.," 5, (1964), pp. 390–394.

*Primary Examiner*—Robert A. Yoncoskie
*Attorney, Agent, or Firm*—Melvin H. Kurtz

[57] ABSTRACT

A process for the interesterification of oils and fats comprising treating said oils and fats with water-soluble microbial lipase enzyme is disclosed.

21 Claims, No Drawings

FAT PROCESS AND COMPOSITION

This is a continuation of application Ser. No. 846,303, filed Oct. 28, 1977, now abandoned, which is a continuation of Ser. No. 766,117, filed Feb. 7, 1977, also abandoned.

SUMMARY OF THE INVENTION

The invention relates to a process for the modification of fats and glyceride oils especially for edible purposes, to improve their characteristics for organoleptic or dietetic reasons by interesterification, using as the interesterification catalyst a lipase enzyme in the presence of a small amount of water sufficient to activate the enzyme. The fatty reactants in the process may comprise glycerides in single or mixed fats and oils and may include free fatty acids also participating in the reaction as in conventional interesterification processes. By the use of selectively active enzymes the invention also provides novel selectively interesterified fats and glyceride oils, particularly novel hardened fats, without elaidinising the fats, which while being unsaturated to a limited degree for confectionery purposes are substantially free from saturated acid radicals in the 2-position as in cocoabutter glycerides.

GENERAL DESCRIPTION

The invention relates to interesterification of fats and glyceride oils and has for its object the provision of improved fats particularly for edible purposes.

Fats and glyceride oils used in edible products consist almost entirely of triglycerides of fatty acids, with a relatively small amount of free fatty acid and partial glycerides. An element of unsaponifiable matter such as sterols may also be present. The physical behaviour of fats particularly melting characteristics are of great importance and are largely determined by the nature and rearrangement of fatty acids on the glycerides constituting the fats. Natural fats may contain a wide variety of fatty acids and the interaction of their glycerides may be highly complex, affecting the physical properties of the fats and oils in very subtle ways. Broadly speaking however the more highly unsaturated and shorter chain acids confer lower-melting characteristics.

Attempts to improve the melting characteristics of fats and glyceride oils have therefore been concerned with replacing the fatty acid radicals of the glycerides they contain by others. This has largely been carried out by interesterification and hydrogenation in hardening processes, although replacement by polyunsaturated acids, usually linoleic acid, has assumed increasing importance on account of the valuable dietetic characteristics of these acids. Both these conventional processes which are catalysed by metals or their compounds are however non-selective in affecting the acid radicals on all the positions of the glyceride molecules. The present invention provides a process for the interesterification of glyceride fats and oils using as interesterification catalyst a lipase enzyme dispersed is the glycerides with a little water to activate the enzyme. Since certain enzymes react selectively for example in affecting only the acid radicals on the 1- and 3-positions of the glyceride molecule, or in responding only to certain fatty acids or their radicals, they enable a selective interesterification to be carried out which will leave specified positions of the glycerides unaffected. One object of the invention is therefore the provision of selectively interesterified fats and oils, particularly where these are hardened by selective substitution of a saturated, if necessary longer chain fatty acid for confectionery or other purposes as a substitute for natural and usually expensive fats rich in disaturated symmetrical glycerides. They may be made without the simultaneous formation of trans-acids which do not occur in nature but which are invariably produced by metal-catalysed hydrogenation processes for hardening fats and oils.

PRIOR ART

Interesterification as a means of modifying the properties of fats and glyceride oils for use in confectionery fats, margarine and culinary fats generally, is well-documented, for example in British Pat. Nos. 590,731, 1,020,826 and 1,143,143, U.S. Pat. Nos. 2,442,536 and 7, 2,875,067 and 3,328,439. A variety of catalysts is known based on alkali or alkaline earth metals.

Lipase enzymes are known in lipolysis reactions in which in the presence of substantial quantities of water partial glycerides are formed, as disclosed for example in J. of Gen. Applied Microbiology 10, 13 (1964). The use of lipases is also discussed in U.S. Pat. Nos. 2,403,413 and 3,652,397. Their principal application is however in fermentation processes as disclosed in U.S. Pat. Nos. 3,619,327 and 3,634,195, again requiring the presence of substantial amounts of water, as also in the pancreatic lipolysis of glycerides discussed by Bergstrom in Biochem. Biophys. 13 page 491 et seq (1954), who also discloses the exchange of free fatty acid with glyceride fatty acids during lipolysis.

This invention relates to fats particularly for edible purposes and their preparation by interesterification.

The rearrangement by interesterification of fatty acid radicals among triglyceride molecules is widely applied to meet the requirements, particularly the melting requirements, for fats, including glyceride oils, particularly for such edible applications as margarine and bakery applications.

The present invention proposes the use as the catalyst in interesterification reactions of a lipase. Accordingly, the present invention provides a process for the interesterification of fats which is characterized by the fact that reaction is carried out in the presence as catalyst of lipase and a small amount of water, which may contain a buffer, to activate the lipase.

The process of the invention is carried out at moderate temperatures, at which the enzyme is active and under mild conditions which avoid the need for strongly acidic or alkaline or other extreme conditions. Preferred temperatures are between 20° and 60° C., particularly up to 50° C., according to the capacity of the enzyme adopted to withstand elevated temperatures. The reaction is in the liquid phase and may be facilitated by dissolving the reactants in an organic solvent, preferably low-boiling alkanes, e.g. petroleum ether (60°–80° C. B range). The solvent should not affect the enzyme.

In contrast to conventional interesterification processes where even 0.1% water is undesirable, requiring additional amounts of the catalyst, a small amount, usually up to 10% but preferably 0.2 to 1% water or buffer solution is necessary for the enzyme to function and excessive precautions to dry the fat or other materials used in the process are therefore not required since any moisture they contain may contribute to the water required in the reaction. More than 1% water or buffer is less desirable in the present invention as the reverse hydrolysis reaction is thereby promoted, with the formation of partial glycerides.

The water required in the reaction may be incorporated into the reaction medium adsorbed on a support agent such as kieselguhr, which may be used to aid dispersion also of the enzyme and, as explained later, preferably combined with the enzyme. Quantities are based on the weight of fatty reactants. The purpose of the buffer is to maintain the reactants at a pH at which the lipase is reactive.

The process of the invention can be applied to achieve the results of conventional interesterification processes.

Free fatty acid may be added to glyceride mixtures to contribute to the formation of glycerides in the rearrangement, together with other fatty acids liberated from the triglycerides themselves in the course of the reaction. Preferably a molar ratio of 0.3:1 to 7:1 acids to glycerides is used according to the extent of reaction required. A further advantage which the present invention provides is due to the specific reactivity of certain lipase enzymes. Whereas some will rearrange the fatty acid radicals on any position of the triglyceride molecule, others react only to change the radicals occupying specified positions, while yet others are reactive only to specific fatty acid species. For example, *Candida cylindracae* lipase is non-specific and provides a true randomisation of all fatty acid radicals on all the glyceride positions, whereas Rhizopus enzymes are specific to the 1,3 terminal acid radicals, giving very little change in any 2-position acid radicals. *Geotrichum Candidum* lipase on the other hand is specific to acids with a double bond in the 9-position, e.g. oleic and linoleic acids, regardless of their position on the glyceride radical.

Again, since the process of the invention usually takes from 20 to 72 hours to complete, according to conditions, less with fixed catalyst beds, it is possible to halt reaction at any stage before a reaction is complete thus giving a further control in the modification of fats which has not hitherto been available in more rapid interesterification reactions.

A widely ranging facility is therefore provided by combining the variables applicable to the invention, for obtaining a wide range of products with the advantages outlined.

The invention may be used to upgrade fats for a wide variety of purposes. For example more highly unsaturated acids may be replaced in glycerides by less unsaturated or saturated acids and vice versa, according to requirements. Again, the exchange may be effected in specific positions of the glyceride residue and/or by specific acids by using enzymes of specific reactivity. Combinations of these various aspects of the invention may be adopted to achieve particular products with a notable decrease in the production of less desired glyceride fractions, thereby simplifying the separation of the required glyceride species from the product mixture and increasing their yield.

An important application of the upgrading of fats and glyceride oils by selective replacement of fatty acid residues in their glyceride molecules in accordance with the invention is in the provision of replacement fats for cocoabutter in the confectionery trade from less expensive vegetable oils and fats. Cocoabutter itself contains substantial quantities of 2-oleyl glycerides of palmitic and stearic acid and these confer the valuable melting characteristics for which the fat is so highly prized, providing in chocolate confectionery a sharp melting in the region of body temperature, from a hard solid resisting melting by handling to a mobile fluid flowing easily and quickly from the tongue. A few alternative sources of vegetable butters, notably shea fat and illipe are of similar constitution, but are themselves expensive and being largely uncultivated are of variable quality. Palm oil is much cheaper and contains significant amounts of dipalmityl 2-unsaturated glycerides and these are recovered by fractionation. The bulk of the glycerides of most vegetable oils however are unsaturated in at least one of the alpha-positions in addition to the beta or 2-position. Attempts to upgrade these glyceride oils for the production of chocolate fats therefore require the specific replacement of 1,3 outer, unsaturated fatty acid radicals by saturated acids to harden the product, particularly stearic acid, and where necessary also of any highly unsaturated acid radicals on the inner, 2-position by the oleyl radical. Both hydrogenation and conventional interesterification processes which may be used for this purpose in hardening processes are however non-selective in affecting all the glyceride positions. Moreover, hydrogenation processes are invariably accompanied by isomerisation of any unsaturated acid radicals remaining in the product from the natural cis-form to the trans-form, for example oleic acid to its isomer elaidic acid. This isomerisation confers a different melting point on a glyceride containing a transacid radical, the amount formed varying according to the catalyst and the reaction conditions, greatly adding to the complexity of the reaction and the uncertainty of the characteristics of the product. By the use of selective lipase the present invention provides selectively interesterified fats and a hardening process which is free from these defects, enabling unsaturated acids or short-chain saturated acids in the 1- and 3-positions to be replaced by saturated acids conferring improved melting characteristics on the product. The invention therefore provides as products hardened mixtures, free from elaidinisation, of glycerides of fatty acids, preferably from $C_{12}$ to $C_{22}$ and more particularly of $C_{16}$ and $C_{18}$ saturated fatty acids. The hardened fats of the invention are good cocoabutter replacements and preferably have an Iodine Value of 25 to 40, reflecting a composition corresponding to an average in each glyceride molecule of a single monoethylenically-unsaturated acid residue. This is in the 2-position and the preferred hardened but still unsaturated fats of the invention are therefore substantially free from saturated acids in the 2-position.

The invention is moreover applicable to upgrading fats by increasing the degree of unsaturation. This may be desirable for dietetic reasons, fully unsaturated fats being prized for their dietetic value. The replacement for this purpose may be particularly by linoleic acid and by the use of positionally-selective lipase catalysts, may be confined to either the outer or inner glyceride positions.

The upgrading of fats in accordance with the invention, whether by hardening or by increasing polyunsaturated acid content, is valuable for confectionery, margarine and culinary fats. In the former, preferably hardened fats contain at most 42% total unsaturated fatty acids more than 85% of those which are in the 2-position being unsaturated.

The enzyme catalyst may be from animal, vegetable or microbial sources, preferably the latter. Commercially available enzyme compositions may be suitable. These are provided as powdered solids, incorporating protein and sugar materials and salts in addition to varying amounts of the active enzyme and preferably contain the equivalent to 1 to 500 units of activity/mg, based on the standard generally adopted of 1 unit releasing 1 micro mole of fatty acid from olive oil substrate in 1 minute under standard conditions. According to these, the olive oil is dispersed to form a 5% emulsion in a 5% aqueous emulsion of gum arabic containing 50 μM calcium chloride, the pH of the reaction being 6.0 and the temperature 37° C. Preferably from 0.02 to 7% of these enzyme compositions are used by weight of fatty reactants.

The reagents comprising fatty reactants including glyceride, water including buffer if desired, and enzyme, are preferably agitated together throughout the reaction to maintain the enzyme dispersed, preferably in a closed vessel to prevent the ingress of moisture. Dispersion of the water and enzyme may be facilitated by including in the reagents an adsorbent, inert powder, for example a filter aid such as e.g. kieselguhr which adsorbs the water and attaches to the enzyme, preferably in an amount from 1% to 10% of the fatty reactants, i.e. fat or oil and their fatty acid.

In many cases a small amount of free fatty acid and partial glycerides may be formed by hydrolysis. These may be removed, together with any surplus free fatty acid by conventional means including liquid-liquid extraction, alkali neutralisation or vacuum or molecular distillation. Silicic acid chromatography is also suitable. Partial glycerides may also be removed by crystallisation or absorption e.g. on silica.

The purified glyceride product may be subjected to solvent fractionation or other conventional processes to recover preferred components as required. The economy of the process may be also improved by enzyme recovery and re-use or by use in fixed beds, particularly if it is carried on a support agent. Enzymes supported on a wide variety of inert materials, usually in finely-divided form, for recovery and re-use are well known. Such materials include carbon, cellulose, glass, Celite, alumina and silica-based adsorption agents, hydroxylapatite, especially in bead form and synthetic resins. These may be used as described to aid dispersion of water and enzyme. Enzymes can also be stabilised for re-use in an insoluble form. Such techniques are well known in enzyme technology, for example in amino acid manufacture and in the production of fructose syrup from glucose.

The invention may be applied to rearrangement of fatty acids commonly occurring in fats, e.g. acids of comparatively short chain length from $C_6$ to $C_{14}$, or of longer chain acids e.g. $C_{16}$ to $C_{18}$ or even longer, e.g. $C_{20}$ or $C_{22}$, and they may be unsaturated with one or more ethylenic bond, whether cis or trans-isomerised, or they may be saturated.

The fatty reagents of the invention comprise these acids whether in free form or combined in glycerides. The invention may be applied to glycerides in animal, marine and vegetable fats and oils. These chiefly comprise glycerides of $C_{16}$ and $C_{18}$ fatty acids, but include those of shorter and longer chain acids, for example lauric fats, crucifera oils. Particular examples of vegetable oils include palm, cottonseed, olive, soyabean and sunflower oils and their derivatives. Vegetable butters are also suitable including in particular shea and illipe.

EXAMPLE 1

25 gms each of coconut oil and olive oil were stirred in a closed vessel at 40° C. for 66 hours with 5% of their weight of Celite and approximately 2.5% of their weight of *Candida cylindracae* lipase (1200 mgms equivalent to 45,000 units) and 0.7% of a 20 millimolar buffer solution of X-trishydroxymethyl methyl-2-aminoethane sulphonic acid at pH 6.5. The reaction mixture obtained was centrifuged and the oil layer decanted, leaving a pellet which was washed with 80 vol.% of the original oil mixture, using a petroleum ether of boiling fraction 40° to 60° C., washings being added to the oil layer.

After removing the solvent by evaporation a reaction product was obtained in 96% yield of the original oil mixture.

A portion of the reaction product was analyzed by application to a silicic acid thin layer plate which was solvent-developed using as developing solvent 60 parts of petroleum ether (40°-60° C. fraction), 40 parts of diethyl ether and 1 part of formic acid. From the plate 72% of a triglyceride range was obtained together with 16.5% of diglyceride, 0.5% monoglyceride and 10.3% free fatty acid.

The composition of the triglyceride fraction was determined by gas liquid chromatography and is compared in Table 1 with that of the original coconut oil/olive oil mixture and the same mixture when interesterified in the presence of a conventional alkali metal catalyst.

TABLE 1

| Triglyceride carbon no. (excl. glycerol residue) | Wt % triglyceride | | |
|---|---|---|---|
| | | Interesterified oil | |
| | In oil | by enzyme | by alkali metal catalyst |
| 20 | 0.1 | 0.1 | 0.3 |
| 28 | 0.3 | 0.2 | 0.5 |
| 30 | 1.1 ⎫ | 0.5 ⎫ | 0.7 ⎫ |
| 32 | 5.0 ⎪ | 1.4 ⎪ | 2.1 ⎪ |
| 34 | 6.7 ⎬ 28.8 | 2.1 ⎬ 14.9 | 2.1 ⎬ 15.4 |
| 36 | 8.4 ⎪ | 4.2 ⎪ | 4.0 ⎪ |
| 38 | 7.6 ⎭ | 6.7 ⎭ | 6.5 ⎭ |
| 40 | 4.5 ⎫ | 7.2 ⎫ | 6.6 ⎫ |
| 42 | 3.4 ⎪ | 13.1 ⎪ | 12.6 ⎪ |
| 44 | 1.9 ⎬ 12.0 | 11.6 ⎬ 60.9 | 11.4 ⎬ 60.9 |
| 46 | 1.2 ⎪ | 11.6 ⎪ | 11.7 ⎪ |
| 48 | 1.0 ⎭ | 17.4 ⎭ | 18.0 ⎭ |
| 50 | 4.7 | 6.8 | 7.4 |
| 52 | 21.2 ⎫ | 7.4 ⎫ | 7.2 ⎫ |
| 54 | 31.8 ⎬ 58.7 | 9.3 ⎬ 23.9 | 8.4 ⎬ 23.5 |
| 56 | 1.0 ⎭ | 0.4 ⎭ | 0.5 ⎭ |
| Total | 99.9 | 100 | 100 |

Substantial change of composition occurs between carbon numbers 40 and 48, from the higher and lower carbon numbers, as a result of interesterification. This is exhibited both by the enzyme-catalyzed and alkali-metal-catalysed processes. The particular oils selected in this Example show the effect of interesterification particularly well, since on the one hand the fatty acid residues of coconut oil are predominantly of lauric and lower fatty acids, whereas on the other hand those of olive oil are predominantly of $C_{18}$ acids.

EXAMPLE 2

2.5 parts of mid-fraction of palm oil, 1.5 parts of stearic acid, 0.25 parts of Celite and 0.004 parts of *Rhizopus delemar* lipase (200 units/mgm), were all stirred together in a closed vessel with 8 parts of petroleum ether of boiling range 60° to 80° C. and 0.02 parts of the buffer described in the previous Example, at 40° C. The enzyme was ex Seikagaku Kogyo.

After 48 hours the mixture obtained was diluted with 10 parts of petroleum ether of boiling range 40° to 60° C., and centrifuged. The solvent was removed by evaporation and the residue analysed as before by thin layer chromatography, recovering a triglyceride fraction, the fatty acid composition of which was determined by gas liquid chromatography and is compared with that of the palm mid-fraction starting material in Table 2. The triglyceride was also subjected to treatment with pancreatic lipase, showing that 98% of the incorporated stearate residues were present in the 1- and 3-positions of the triglyceride molecules.

Particulars of the fatty acid distribution in the original palm mid-fraction and triglyceride product in Table 2 appear with similar details for comparison of the following Examples of which Example 2 was repeated using a supported enzyme, *A. niger* in Example 3, *R. arrhizus* in 4 and *R. japonicus* in 5.

The procedure for preparing the supported enzyme was as follows:

2 parts (7200 U/gm) of the lipase were dissolved in 20 parts of distilled water and 5 parts Celite added with stirring at 0° C. 30 parts acetone were then added over 5 minutes and stirring continued for 30 minutes more. The solid product formed was filtered off and dried at 20° C. under reduced pressure.

0.25 parts of the Celite lipase (1028 U/gm) powder were used in the reaction which otherwise was carried out as before.

The origins of the lipase material used were as follows:

*A. niger*: Amano Pharmaceutical Co., Japan;
*R. arrhizus*: Soc. Rapidase, France;
*R. japonicus*: Nagase & Co. Ltd., Japan.

TABLE 2

| Triglyceride | Lipase | Fatty Acid | | | | |
|---|---|---|---|---|---|---|
| | | 14:0 | 16:0 | 18:0 | 18:1 | 18:2 |
| PMF | | 0.8 | 58.7 | 6.6 | 31.2 | 2.7 |
| EXAMPLE | | | | | | |
| 2 | R. delemar | 1.0 | 37.4 | 29.6 | 30.0 | 2.0 |
| 3 | A. niger | 0.3 | 34.8 | 30.9 | 31.5 | 2.5 |
| | | (0.0 | 16.1 | 2.7 | 77.6 | 3.6) |
| 4 | R. arrhizus | 0.3 | 37.4 | 30.5 | 29.8 | 2.0 |
| 5 | R. jeponicus | 0.3 | 37.2 | 32.3 | 28.6 | 1.6 |

The marked increase in stearic acid content of the triglyceride products provided by each lipase is apparent, with no substantial change in the oleic or linoleic content. Significant decrease in palmitic acid content is also evident.

The data in parenthesis for Example 3 refers to analysis of the acids occupying the 2-position. From this the amount of individual triglyceride species in the triglyceride product recovered was calculated using van der Wal & Coleman's hypothesis (J.A.O.C.S. 37 18 (1960) and 40 242 (1963) and Adv. Lipid Res. I, 1 (1963)). Results appear in Table 3 and are compared with corresponding data for palm mid-fraction.

TABLE 3

| Triglyceride species | PMF | Interesterified triglyceride % |
|---|---|---|
| POP | 57 | 18.7 |
| POSt | 13 | 36.7 |
| StOSt | 1 | 17.0 |
| Other glycerides | 29 | 27.6 |

St = Stearyl

From Table 3 it is evident that a marked increase in the amount of combined stearic acid occurs in the 2-oleyl symmetrical disaturated glycerides obtained in the product, the major part being palmitostearyl 2-oleyl glyceride.

Analysis of the 2-position of the triglyceride products from the Examples in Table 2 showed that 95–97% stearic acid radicals incorporated assumed the 1,3-positions, with substantially no removal of oleic acid radicals from the 2-position.

Example 3 was repeated at 50° and 60° C., yielding triglycerides containing 32.9% and 27.6% combined stearic acid respectively.

EXAMPLE 6

Example 3 was repeated except that the enzyme powder was also recovered and re-incubated several times with fresh starting materials. These were 2.5 parts each stearic acid and palm oil with water instead of buffer.

TABLE 4

| Fatty acid | in palm oil | Wt % fatty acid in interesterified triglyceride Incubation | | | | | |
|---|---|---|---|---|---|---|---|
| | | 1 | 2 | 3 | 4 | 5 | 6 |
| 14:0 | 1.0 | 0.5 | 0.5 | 0.3 | 0.4 | 0.3 | 0.5 |
| 16:0 | 45.1 | 24.0 | 24.8 | 24.7 | 28.1 | 29.5 | 29.8 |
| 18:0 | 5.1 | 38.1 | 38.3 | 40.3 | 34.8 | 31.5 | 30.9 |
| 18:1 | 39.3 | 29.6 | 29.2 | 28.1 | 29.6 | 31.0 | 31.1 |
| 18:2 | 9.5 | 7.6 | 7.2 | 6.6 | 7.1 | 7.7 | 7.7 |
| Incubation time (days) | | 2 | 2 | 3 | 2 | 2 | 3 |
| Parts of water added | | 0.020 | 0.020 | 0.015 | 0.015 | 0.010 | 0.015 |

As shown in Table 4, less water was added later to avoid possible build-up. The time for each cycle was varied only for convenience, conversion being substantially maintained throughout the Example.

EXAMPLE 7

2.5 parts palm mid-fraction were reacted for 2 days at 40° C. with 0.75 parts each of stearic and arachidic acid, dissolved in 10 parts petroleum ether (60°–80° C. boiling range) by agitation with 0.25 parts *Asp. niger* lipase/kieselguhr powder, prepared as described in Example 2 and previously wetted by shaking for 30 minutes with 0.02 parts water in a sealed tube.

The fatty products were composed of 47% triglyceride, 11% diglyceride and 42% free fatty acid with less than 1% monoglyceride. The triglyceride contained as % saturated acids $C_{14}0.3$; $C_{16}31.3$; $C_{18}19.5$; $C_{20}15.2$ and 30.0 oleic and 3.7 linoleic acids. Analysis of the acids in the 2-position by pancreatic lipase treatment showed that 97% of the stearic and arachidic residues incorporated into the triglyceride product occupied 1- and 3-positions.

EXAMPLE 8

*Candida cylindracae* lipase ex Meito Sangyo Company Limited was precipitated with acetone onto kieselguhr by the method described in Example 2. 2.5 parts of olive oil and 1.5 parts linoleic acid were dissolved in 8 parts of 60°–80° C. petroleum ether and the solution reacted with agitation for 2 days at 40° C. with a mixture of 0.137 parts of the supported lipase and 0.113 parts kieselguhr, previously wetted with 0.02 parts of water as described in Example 7. After recovery the product contained 50% triglyceride, 11% diglyceride, 39% free fatty acid and less than 1% monoglyceride. The fatty acid composition of the interesterified triglyceride is compared in Table 5 with the original olive oil.

TABLE 5

| | Fatty Acid wt % | |
| --- | --- | --- |
| | Olive oil | Interesterified triglyceride |
| 16:0 | 11.5 | 7.9 |
| 16:1 | 0.2 | 0.1 |
| 18:0 | 1.8 | 2.7 |
| 18:1 | 77.2 | 55.1 |
| 18:2 | 9.3 | 34.2 |

77% of the incorporated linoleate residues of the triglyceride product were found by analysis to occupy the 1- and 3-positions, compared with 95–98% obtainable with lipases showing positional specificity. In theory fully non-specific reaction should give 67% incorporation into the 1- and 3-positions.

EXAMPLE 9

A mixture of equal parts of shea butter and palm mid fraction was dissolved in its own weight of 60°–80° petroleum ether and reacted for 2 days at 40° C. with 0.25 parts of an *A. niger* lipase precipitated on kieselguhr as described in Example 2 and wetted before use with 0.02 parts of water as described in Example 7. After recovery the triglyceride fraction of the product exhibited a substantial drop, from 37.8% to 18%, of triglycerides of carbon number 50, and a corresponding increase, from 18.5 to 43.7, of those of carbon number 52. A similar change, from 39.1 to 33.3%, was observed for triglycerides of carbon number 54. Little change in carbon number occurred below or above those indicated. Determination of the fatty acid compositions showed that from a total of 91.1% unsaturated acid in the 2-position of the starting triglyceride, a decrease only to 87.3% was observed in the corresponding position of the interesterified product, indicating that this position had participated scarcely at all in the interesterification, and hence the highly specific nature of the enzyme. Comparison with the change in carbon number indicates a substantial shift in 2-oleyl disaturated triglycerides, from a mixture of distearyl and dipalmityl glycerides, to the corresponding 2-oleyl palmityl stearyl glyceride. This was confirmed by the composition of the various triglyceride species, calculated by the above-mentioned hypothesis and compared with the starting material. Change in triglycerides from starting material to the product triglycerides was as follows: POP 26–13, POSt 9–22, StOSt 17–9, others 48–56, all percentages.

EXAMPLE 10

2½ parts of olive oil and 1 of erucic acid, dissolved in 2 parts of 60–80 petroleum ether were reacted for 3 days at 30° C. with 0.25 parts of the *A. niger* lipase precipitated and wetted as before with 0.02 parts of water. From the product 55% triglyceride, 11% diglyceride, 34% free fatty acid and traces of monoglyceride were recovered and separated. Pancreatic lipase analysis of the 2-position showed that 95% of the erucate residues present were in the 1- and 3-positions. The amount of monounsaturated $C_{20}$ and $C_{22}$ acids increased from nil in the olive oil to 0.8 and 24.8 respectively in the triglyceride product, the principal additional changes being a decrease from 77.2 to 56.3 in the amount of oleic acid present and from 11.5 to 7.8% in the palmitic acid present.

EXAMPLE 11

Example 8 was repeated using as the lipase *Geotrichum Candidum*. This was grown on a medium containing as its principal ingredients yeast extract and olive oil. *G. Candidum* lipase powder was isolated from the resultant broth by ultrafiltration and freeze-drying and then precipitated onto kieselguhr with acetone by the method previously described.

2½ parts of olive oil and 0.75 parts of linoleic acid, dissolved in 4 parts of 60°–80° petroleum ether, were reacted for 3 days at 40° C. with 0.25 parts of the *G. Candidum* bound lipase, previously wetted as described in the above Examples.

In further tests the Example was repeated using either the same amount of stearic acid or the same amount of both acids together. Substantial linoleic acid incorporation took place both in the presence and absence of stearic acid which however itself remained uncombined.

EXAMPLE 12

5 parts of each of shea fat and stearic acid were dissolved in 24 parts of petroleum ether of boiling range 60°–80° C. and reacted for 2 days at 40° C. with 0.5 parts of *A. niger* lipase/keiselguhr powder prepared by precipitation as previously described and 0.01 parts of water. The product contained 34% triglyceride, 9% diglyceride, 54% free fatty acid and traces of monoglyceride and unidentified material, probably gum, terpene esters and etcetera amounting to 3%.

Analysis of the triglyceride product, recovered by molecular distillation, showed an increase in stearic acid residues of approximately 15%, substantially all (97%) of which appeared in the 1- and 3-positions. A decrease of palmitic (approximately 2%), oleic (10%) and linoleic (2%) acid residues also occurred.

EXAMPLE 13

600 gms each of palm oil and commercial stearic acid containing 95.8% C 18:0 were dissolved in 2880 gms of commercial hexane and stirred in a closed vessel to exclude air for 48 hours at 40° C. with 100 gms of kieselguhr powder on which 60 gms of *A. niger* lipase was previously precipitated as described, the composition being previously wetted with 4.8 mls of water.

The powder was removed from the reaction mass by filtration and the hexane evaporated to give 1175 gms of crude interesterified fat mixture.

From a portion subjected to molecular distillation at 185° C. and $4 \times 10^{-2}$ atmospheres, 595.5 gms of a distillate was recovered containing free fatty acid and traces of glycerides, the residue containing 324.8 gms of triglyceride essentially free from fatty acid and 90.6 gms of diglycerides. The fatty acid analysis of the triglyceride fraction of the residue is compared with that of palm oil and the mid-fraction subsequently obtained, in Table 6, in which its triglyceride analysis also appears.

352 gms of the glyceride mixture was fractionated twice by crystallisation from acetone. In the first fractionation the mixture was dissolved in 1216 gms of acetone which was then cooled to 0° C. and held there for an hour, giving a crystallised mass which after filtration and washing twice with 875 mls of acetone each time at 0° C., weighed 201.7 gms. This was recrystallised from 1000.8 gms of acetone at 18° C. and the filtrate combined with 2 washes, each of 88.2 gms of acetone at 18° C. and evaporated to remove acetone from 113.5 gms of mid-fraction, consisting of 91% triglyceride and 9% of diglyceride. The latter was removed by molecular distillation and the triglyceride component of the mid-fraction recovered in 80% yield by molecular distillation for fatty acid analysis as given in Table 6.

The results show that enrichment of the 1- and 3-positions with stearic acid occurs in the reaction mixture and that solvent-fractionation yields a mid-fraction which, compared with palm mid-fraction itself is enriched in stearic acid and consequently in the valuable POSt and StOSt glycerides.

TABLE 6

|  | Composition wt % | | |
|---|---|---|---|
|  | Reaction product | | |
| Fatty Acid | Triglyceride residue | mid-fraction | Palm Oil |
| 16:0 | 23.2 | 20.5 | 44 |
| 18:0 | 38.2 | 44.5 | 5 |
| 18:1 | 30.6 | 30.3 | 40 |
| 18:2 | 8.0 | 4.7 | 10 |
| Triglycerides | | | |
| S - Saturated | | | |
| U - Unsaturated | | | |
| L - Linoleic | | | |
| O - Oleic | | | |
| SSS | 13.4 | | |
| SSO | 4.5 | | |
| SLS | 12.5 | | |
| SUU | 22.5 | | |
| Others | 3.7 | | |
| P - Palmitic | | | |
| St - Stearic | | | |
| StOSt | 17.5 | | |
| POSt | 20.1 | | |
| POP | 5.8 | | |

EXAMPLE 14

Example 13 was repeated using palm mid-fraction instead of palm oil, the hexane solution after filtration being held at 5° C. for an hour, precipitating a mixture of free fatty acids and a glyceride top fraction. After washing and combining the washings with filtrate evaporation of the solvent left a fatty residue consisting of glycerides and free fatty acid, 125 gms of which was submitted to molecular distillation to remove free fatty acid. 75.5 gms of residue were obtained containing 80% triglyceride and 20% diglyceride and were crystallised at 4° C. from 755 gms of acetone, yielding 35 gms of a triglyceride mid-fraction containing 3.4% diglyceride. Comparison of the fatty acid analysis of this mid-fraction product to the starting material showed a substantial fall in palmitic acid from 54% to 23.8% and a corresponding rise, from 6.9% to 44%, in stearic acid content. Small changes in the oleic and linoleic acid content also occurred. The product was shown to contain 79.8% SOS, 2.9% SSO, 5% SSS and 12.3% other glycerides. Physical evaluation was carried out by determination of its stabilised dilatations, measured as described in British Patent Specification No. 827,172 with the following results: $D_{20}$ 1910, $D_{25}$ 1575, $D_{30}$ 985, $D_{32.5}$ 630, $D_{35}$ 325 and $D_{40}$ 130.

These physical data established the suitability of the product for use in confectionery.

EXAMPLE 15

Purified porcine pancreatic lipase was precipatated onto kieselguhr by the method already described for Example 3. The powder obtained exhibited an activity of about 600 Units/gm and 0.35 parts were dispersed with 0.03 parts of water in fatty reactants comprising 2½ parts of a mid-fraction of palm oil and 0.5 parts of myristic acid, dissolved in 4 parts pet. other 60° to 80° C. and agitated at 30° C. The reaction product contained 50% triglyceride, 19% diglyceride, 31% free fatty acid and traces of monoglyceride. The triglyceride fraction was recovered and its fatty acid composition determined. By comparison with the palm mid-fraction starting material, the myristic acid content increased from 0.7 to 10.1%, while a decrease of palmitic acid from 54.2 to 44.9 was observed. No substantial change in $C_{18}$ acids took place. Analysis of the 2-position of the triglyceride showed that 95% of the incorporated myristic residues were present in the 1- and 3-positions.

EXAMPLE 16

0.25 parts of *C. cylindracae* lipase supported on kieselguhr powder and previously wetted with 0.02 to 5 parts of water as described in Example 7, were dispersed in 2.5 parts of olive oil and 0.5 parts octanoic acid and agitated for 2 days at 40° C. The product contained 51% triglyceride, 15% diglyceride, 34% free fatty acid and traces of monoglyceride. The triglyceride fraction was recovered and its fatty acid composition determined. This showed an increase to 7.9% of $C_8$ saturated acid. Only minor changes were found among higher saturated and unsaturated acids, except for 18:1 acid, showing a decrease from 72.8 to 69%.

What is claimed is:

1. A process for the interesterification of glyceride oil or fat, comprising:
   treating said oil or fat with a water-soluble microbial lipase enzyme under conditions to effect an interesterfication reaction, in the presence of up to 10% water wherein said water-soluble microbial lipase enzyme is adsorbed on an inert, powdered, water-insoluble dispersing agent and recovering from the reaction a glyceride product free from fatty acid and partial glycerides.

2. A process according to claim 1 wherein said water is present at a level of 0.2 to 1 percent by weight of said glyceride oil or fat.

3. A process according to claim 1 wherein said water soluble enzyme is present at a level of 0.05 to 5 percent by weight of said glyceride oil or fat.

4. A process according to claim 1 wherein said enzyme is specifically reactive to the 1-, and 3-positions of the glyceride molecule.

5. A process according to claim 1 wherein said enzyme is selected from the group consisting of Rhizopus, Geotrichum and Aspergillus species.

6. A process according to claim 1 wherein said dispersing agent is present at a level of 1 to 10 percent by weight of said glyceride oil or fat.

7. A process according to claim 1 wherein said water soluble enzyme is recovered and re-used in said process.

8. A process according to claim 1 wherein said treatment is at a temperature of 20° to 60° C.

9. A process according to claim 1 wherein said glyceride fat or oil comprises a mid-fraction of palm oil.

10. A process according to claim 1 wherein said glyceride fat or oil comprises a vegetable butter.

11. A process according to claim 1 wherein said enzyme is specifically reactive to fatty acids or the radicals thereof with a double bond in the 9-position only.

12. A process according to claim 1 wherein said enzyme is selected from the group consisting of *Candida cylindracae, Geotrichum candidum, Rhizopus delemar, Rhizopus arrhizus, Rhizopus japonicus* and *Aspergillus niger lipase.*

13. A process according to claim 1 wherein said dispersing agent is selected from the group consisting of diatomaceous earth, activated charcoal, alumina, glass, carboxymethyl cellulose and hydroxyapatite.

14. A process according to claim 1 wherein said glyceride oil or fat is of vegetable origin.

15. A process according to claim 14 wherein said glyceride oil or fat is selected from the group consisting of olive, palm, cottonseed, soybean and sunflower oils.

16. A process of modifying the properities of fats and oils comprising selectively interesterifying the glycerides thereof by:
   treating said fat or oil with a water-soluble microbial lipase enzyme, in the presence of up to 10% water, for a time sufficient to effect said interesterification, wherein said enzyme is selectively specific to the 1- and 3-positions of the glycerides and is adsorbed on an inert, powdered, water-insoluble dispersing agent.

17. A process for the interesterification of glyceride oil or fat comprising:
   treating said fat or oil, in the presence of a free fatty acid, with a water soluble microbial lipase enzyme, in the presence of up to 10 percent water, for a time sufficient to effect said interesterification, wherein said water soluble enzyme is adsorbed on an inert, powdered, water insoluble dispersing agent.

18. A process according to claim 17 wherein the molar ratio of said glyceride oil or fat to free fatty acid is 0.3:1 to 7:1.

19. A process according to claim 17 wherein said free fatty acid comprises stearic acid.

20. A process according to claim 17 wherein said free fatty acid comprises linoleic acid.

21. A process for the preparation of a 1, 3-di-saturated glyceride comprising selectively interesterifying a more highly unsaturated glyceride by treating said glyceride, in the presence of a saturated free fatty acid with a water soluble microbial lipase enzyme, in the presence of up to 10 percent water, for a time sufficient to effect said interesterification, wherein said enzyme is selectively specific to the 1 and 3 positions of the glyceride molecule and is adsorbed on an inert, powdered, water insoluble dispersing agent.

* * * * *